(12) United States Patent
Li et al.

(10) Patent No.: US 10,513,605 B2
(45) Date of Patent: Dec. 24, 2019

(54) HALOGEN-FREE EPOXY RESIN COMPOSITION, PREPREG, LAMINATE AND PRINTED CIRCUIT BOARD CONTAINING THE SAME

(71) Applicant: SHENGYI TECHNOLOGY CO., LTD., Guangdong (CN)

(72) Inventors: Hui Li, Guangdong (CN); Kehong Fang, Guangdong (CN); Yongjing Xu, Guangdong (CN)

(73) Assignee: SHENGYI TECHNOLOGY CO., LTD. (CN)

( * ) Notice: Subject to any disclaimer, the term of this patent is extended or adjusted under 35 U.S.C. 154(b) by 0 days.

(21) Appl. No.: 15/316,880

(22) PCT Filed: Sep. 14, 2016

(86) PCT No.: PCT/CN2016/099121
§ 371 (c)(1),
(2) Date: Dec. 7, 2016

(87) PCT Pub. No.: WO2017/092482
PCT Pub. Date: Jun. 8, 2017

(65) Prior Publication Data
US 2017/0283610 A1    Oct. 5, 2017

(30) Foreign Application Priority Data

Dec. 4, 2015    (CN) .......................... 2015 1 0888933

(51) Int. Cl.
| | |
|---|---|
| *C08L 63/10* | (2006.01) |
| *C08L 35/06* | (2006.01) |
| *H05K 1/03* | (2006.01) |
| *C08G 59/42* | (2006.01) |
| *B32B 15/092* | (2006.01) |
| *C08G 59/40* | (2006.01) |
| *C07D 233/00* | (2006.01) |
| *C07D 265/36* | (2006.01) |
| *C08F 214/28* | (2006.01) |
| *C08J 5/24* | (2006.01) |
| *H05K 1/05* | (2006.01) |
| *B32B 27/38* | (2006.01) |

(Continued)

(52) U.S. Cl.
CPC ............ *C08L 63/10* (2013.01); *B32B 15/092* (2013.01); *B32B 15/20* (2013.01); *B32B 17/04* (2013.01); *B32B 27/18* (2013.01); *B32B 27/20* (2013.01); *B32B 27/26* (2013.01); *B32B 27/302* (2013.01); *B32B 27/38* (2013.01); *C08G 59/40* (2013.01); *C08G 59/4014* (2013.01); *C08G 59/42* (2013.01); *C08G 59/4223* (2013.01); *C08J 5/24* (2013.01); *C08K 3/36* (2013.01); *C08K 5/51* (2013.01); *C08K 5/5399* (2013.01); *C08L 35/06* (2013.01); *C08L 63/00* (2013.01); *H05K 1/03* (2013.01); *H05K 1/0313* (2013.01); *H05K 1/0353* (2013.01); *H05K 1/05* (2013.01); *C07D 233/00* (2013.01); *C07D 265/36* (2013.01); *C08F 214/28* (2013.01); *C08J 2363/00* (2013.01); *C08J 2435/06* (2013.01)

(58) Field of Classification Search
CPC ............... C08L 63/00–10; C08L 35/06; C09D 163/00–10; C09D 135/06; C09J 163/00–10; C09J 135/06; C08J 2363/00–10; C08J 2335/06; C08J 5/24; B32B 15/092; H05K 1/03; H05K 1/0313; H05K 1/0353; C08G 59/00–68
See application file for complete search history.

(56) References Cited

U.S. PATENT DOCUMENTS

| | | | |
|---|---|---|---|
| 9,005,761 B2 | 4/2015 | Lin et al. | |
| 2006/0142542 A1* | 6/2006 | Okada | C07F 9/067 |
| | | | 528/399 |

(Continued)

FOREIGN PATENT DOCUMENTS

| | | |
|---|---|---|
| CN | 102633952 A | 8/2012 |
| CN | 103724944 A | 4/2014 |

(Continued)

OTHER PUBLICATIONS

Huntsman Advanced Materials, Raising Performance with Benzoxazine Resins (Quarter 1, 2015).*

(Continued)

*Primary Examiner* — Kregg T Brooks
(74) *Attorney, Agent, or Firm* — McDonald Hopkins LLC

(57) ABSTRACT

The present invention relates to a halogen-free epoxy resin composition, a prepreg and a laminate containing the same. The halogen-free epoxy resin composition comprises 60 parts by weight of epoxy resin, from 15 to 28 parts by weight of benzoxazine resin, and from 10 to 20 parts by weight of styrene-maleic anhydride. The present invention discloses using from 15 to 28 parts by weight of benzoxazine resin and from 10 to 20 parts by weight of styrene-maleic anhydride to cure 60 parts by weight of epoxy resin, to ensure the Df stability of prepregs at different curing temperature conditions while maintaining low dielectric constant and low dielectric loss. The prepregs and laminates prepared from the resin composition have comprehensive performances, such as low dielectric constant, low dielectric loss, excellent flame retardancy, heat resistance, cohesiveness, low water absorption and moisture resistance, and are suitable for use in halogen-free multilayer circuit boards.

11 Claims, No Drawings

(51) Int. Cl.

| | | |
|---|---|---|
| *B32B 27/18* | (2006.01) | |
| *B32B 27/26* | (2006.01) | |
| *B32B 27/20* | (2006.01) | |
| *B32B 27/30* | (2006.01) | |
| *C08L 63/00* | (2006.01) | |
| *C08K 3/36* | (2006.01) | |
| *B32B 17/04* | (2006.01) | |
| *C08K 5/5399* | (2006.01) | |
| *C08K 5/51* | (2006.01) | |
| *B32B 15/20* | (2006.01) | |

(56) References Cited

U.S. PATENT DOCUMENTS

| | | | | |
|---|---|---|---|---|
| 2011/0045303 A1* | 2/2011 | He | .................... | C08G 59/5073 |
| | | | | 428/418 |
| 2011/0059324 A1* | 3/2011 | He | .................... | B32B 15/20 |
| | | | | 428/457 |
| 2013/0161080 A1* | 6/2013 | Lin | .................... | C08L 79/04 |
| | | | | 174/257 |
| 2014/0128509 A1* | 5/2014 | Chen | .................... | C08L 63/00 |
| | | | | 523/439 |
| 2014/0178696 A1 | 6/2014 | Yu | | |
| 2015/0147799 A1 | 5/2015 | Li et al. | | |
| 2016/0194438 A1* | 7/2016 | Ye | .................... | C08G 59/4261 |
| | | | | 523/439 |

FOREIGN PATENT DOCUMENTS

| | | |
|---|---|---|
| CN | 103937157 A | 7/2014 |
| TW | 200718748 | 5/2007 |
| TW | 201425448 A | 7/2014 |
| WO | 2016119356 | 8/2016 |

OTHER PUBLICATIONS

ISA / CN, International Search Report and Written Opinion, prepared for PCT/CN2016/099121, dated Nov. 28, 2016.

"Epoxy Resins Reactive Flame Retardants Hardeners." Thermosetting Resins. 2016.

"Styrene Maleic Anhydride Copolymer," Total Cray Valley. 2016.

* cited by examiner

HALOGEN-FREE EPOXY RESIN COMPOSITION, PREPREG, LAMINATE AND PRINTED CIRCUIT BOARD CONTAINING THE SAME

CROSS-REFERENCE TO RELATED APPLICATION

This application is a 35 U.S.C. 371 national stage filing of PCT Application No. PCT/CN2016/099121, filed on Sep. 14, 2016, which claims priority to Chinese Patent Application No. 201510888933.3, filed on Dec. 4, 2015, both of which are incorporated herein in their entirety by reference.

TECHNICAL FIELD

The present invention belongs to the technical field of copper-clad laminates, specifically relates to a halogen-free epoxy resin composition, a prepreg, a laminate and a printed circuit board containing the same.

BACKGROUND ART

Currently, halogen-containing flame retardants (especially brominated flame retardants) are widely applied in macromolecular flame retardant materials, and have a better flame retardant effect. With the improvement of people's awareness of environmental protection and the promulgation of a series of EU directives, the development of halogen-free flame retardant printed wiring boards has become a key point in the industry. The manufacturers of copper-clad laminates all launch their own halogen-free flame retardant copper-clad laminates.

Phosphorus-containing resins are generally used in the current industry to realize the flame retardant effect. However, too much phosphorus introduction will make the substrate have a high water-absorption, a worse chemical resistance and the like.

In recent years, benzoxazine as matrix resin for the development of halogen-free substrate has drawn more attention. Benzoxazine is a benzo six-membered heterocyclic system consisting of oxygen atoms and nitrogen atoms, and has a feature of ring-opening polymerization. During the polymerization, no micromolecule is released; after the polymerization, a reticulate structure like phenolic resin is formed. The product has a small curing shrinkage, a low porosity, excellent mechanical, electrical and flame retardant properties.

On the other hand, electronic products are developed in the direction of lightness, thinness, shortness, high densification, securitization and high functionalization along with rapid development of electronic industry, which imposes higher performance requirements on the printed circuit boards as a carrier. With the high speed and multi-functionalization of information processing of electronic products, and the continuous improvement of application frequency, the requirements on the dielectric constant and dielectric loss will become lower, besides maintaining higher requirements on the heat resistance of the laminate materials.

The current conventional FR-4 cannot satisfy the use requirements on high frequency and rapid development of electronic products. Meanwhile, the substrate materials, together with electronic components, will become one important route for the designers of PCB and terminal manufacturers to improve the product performances, rather than play a role of traditional mechanical support any more. High Dk will slow the signal transmission rate, and high Df will partially transform the signal to thermal energy and loss in the substrate materials. Thus high frequency transmission having a low dielectric constant and a low dielectric loss, especially the development of halogen-free high frequency plates, has become a key point of the industry of copper-clad laminates.

In order to solve the aforesaid problems, CN101684191B discloses obtaining a cured product having a lower dielectric constant and dielectric loss by co-curing epoxy resin with benzoxazine, styrene-maleic anhydride (SMA) and phosphorus-containing curing agent. Although too much SMA can reduce the dielectric constant of the material, there will be other unavoidable problems, especially notable effect on cohesiveness. This is because non-polar styrene structural units in SMA molecular structure decrease the polarity of the modified matrix resin and weaken the interaction force between resins and copper foils. Meanwhile, plenty of benzene ring structures in SMA increase the fragility of resin cross-linked network, which will have adverse effect on the cohesiveness under dynamic conditions, so as to reduce the binding strength between the substrates and between the substrates and copper foils. Along with the development of electronic industry, higher requirements on heat resistance of substrates are put forward.

CN100523081C discloses co-curing phosphorus-containing and halogen-free, phosphorus-free epoxy composition with benzoxazine, styrene-maleic anhydride and other curing agents to obtain a cured product having a lower dielectric constant and dielectric loss. Although phosphorus-containing epoxy as the matrix resin can achieve excellent flame retardant, the introduction of too much phosphorus will necessarily have a great effect on the water absorption of the substrate, and have adverse effect on many performances of the substrate.

CN103131131A discloses co-curing epoxy resin with benzoxazine, styrene-maleic anhydride and amine curing agent to obtain a cured product having a lower dielectric constant and dielectric loss. Although the introduction of amine curing agent can increase the cohesiveness of the substrate, the heat resistance of the substrate will necessarily be reduced, which cannot meet the requirements on high multi-layer applications.

CN 103881302A discloses a resin composition and copper foil substrate and printed circuit board using the same. The resin composition comprises epoxy resins, benzoxazine resins, styrene-maleic anhydride copolymers and polyesters. Although polyesters have better dielectric properties, they have a high price. Moreover, too much benzoxazine is used in the resin composition, which will increase the fragility of the substrate.

Moreover, the prior art above of co-curing epoxy resins with benzoxazine and styrene-maleic anhydride does not consider the effect of the usage amounts of benzoxazine and styrene-maleic anhydride on the dielectric loss value (Df) stability of the prepreg under different curing temperature conditions. Stable Df value has an important meaning to the stable transmission of signals in the terminal application of substrates.

DISCLOSURE OF THE INVENTION

In view of the shortcomings of the prior art, one object of the present invention lies in providing a halogen-free epoxy resin composition, which, by controlling the amounts of benzoxazine and styrene-maleic anhydride (SMA) within suitable ranges, ensures Df value stability of prepregs under different curing temperature conditions while maintaining a low dielectric constant and a low dielectric loss, and overcomes the current shortcomings that Df of benzoxazine and styrene-maleic anhydride-cured epoxy resin system changes along with the curing temperature.

In order to achieve the aforesaid object, the present invention discloses the following technical solution.

A halogen-free epoxy resin composition, comprising 60 parts by weight of epoxy resin, from 15 to 28 parts by weight of benzoxazine resin, and from 10 to 20 parts by weight of styrene-maleic anhydride.

By choosing 15-28 parts by weight of benzoxazine resin and 10-20 parts by weight of styrene-maleic anhydride to cure 60 parts by weight of epoxy resin, the present invention ensures the Df value stability of the prepreg under different curing temperature conditions, and overcomes the shortcomings that the Df of the benzoxazine and styrene-maleic anhydride-cured epoxy resin system changes along with the curing temperature, while maintaining a low dielectric constant and a low dielectric loss.

Benzoxazine resin is advantageous to improve the flame retardant function, hygroscopicity, heat resistance, mechanical performance and dielectric performances of the cured resins and the substrates obtained therefrom. By choosing the addition amount, the present invention also ensures the Df value stability of the prepreg under different curing temperature conditions, and overcomes the shortcomings that the Df of the benzoxazine and styrene-maleic anhydride-cured epoxy resin system changes along with the curing temperature, while the substrates have the aforesaid performances. In the present invention, the benzoxazine resin is in an amount of, e.g. 16, 17, 18, 19, 20, 21, 22, 23, 24, 25, 26, 27 or 28 parts by weight. If the benzoxazine resin is added in an amount less than 15 parts by weight, Tg and dielectric performances thereof are poor; if the amount thereof goes beyond 28 parts by weight, the fragility of the substrate will increase, and the Df value will change along with the curing temperature and have a reduced stability. Preferably, the benzoxazine resin is added in an amount of 20-25 parts by weight.

In the present invention, the styrene-maleic anhydride is added in an amount of, e.g. 10, 11, 12, 13, 14, 15, 16, 17, 18, 19 or 20 parts by weight. The styrene-maleic anhydride in the present invention is advantageous to improve the dielectric performances of the substrates. The amount of the styrene-maleic anhydride added within the range of 10 to 20 parts by weight can make the halogen-free epoxy resin composition have a better comprehensive performance. If the styrene-maleic anhydride is added in an amount less than 10 parts by weight, the substrate has a low Tg and cannot improve the dielectric performances; if the amount thereof goes beyond 20 parts by weight, the cohesiveness and flame retardancy of the substrate will get worse, and the Df value of the substrate will change along with the curing temperature, so that the stability of the Df value will be reduced. Preferably, the styrene-maleic anhydride is added in an amount of 15-18 parts by weight.

The halogen-free epoxy resin composition comprises 60 parts by weight of epoxy resin, from 20 to 25 parts by weight of benzoxazine resin, and from 15 to 18 parts by weight of styrene-maleic anhydride.

Besides the aforesaid performances, the substrates obtained from such preferable halogen-free epoxy resin composition further have a lower Df value and a higher Tg.

The halogen-free epoxy resin composition further comprises a phosphorus-containing flame retardant.

The phosphorus-containing flame retardant comprises a phosphorus-containing novolac and a phosphorus-nitrogen based compound.

The phosphorus-containing flame retardant comprises from 10 to 40 parts by weight of a phosphorus-containing novolac and from 10 to 50 parts by weight of a phosphorus-nitrogen based compound.

In the present invention, the phosphorus-containing novolac is in an amount of, e.g. 10, 11, 14, 17, 20, 23, 26, 29, 32, 35 or 38 parts by weight. When the phosphorus-containing novolac is in an amount less than 10 parts by weight, the flame retardancy cannot reach the V-0 level; when the amount thereof is higher than 40 parts by weight, the substrate has an increased water absorption and a reduced Tg, though the flame retardancy can be ensured, and the PCT performance of the substrate will be affected.

In the present invention, the phosphorus-nitrogen based compound is in an amount of, e.g. 10, 11, 14, 17, 20, 23, 26, 29, 32, 35, 38, 41, 44, 47 or 49 parts by weight. When the phosphorus-nitrogen based compound is added in an amount less than 10 parts by weight, it has a poor flame retardancy; when the amount thereof goes beyond 50 parts by weight, the cost increases, and the substrate has a reduced glass transition temperature.

In the present invention, the epoxy resin is anyone preferably selected from the group consisting of bisphenol A epoxy resin, bisphenol F epoxy resin, biphenyl epoxy resin, alkyl novolac epoxy resin, dicyclopentadiene epoxy resin, bisphenol A novolac epoxy resin, o-cresol novolac epoxy resin, phenol novolac epoxy resin, tetrafunctional epoxy resin, isocyanate-modified epoxy resin, naphthalene epoxy resin and phosphorus-containing epoxy resin, or a mixture of at least two selected therefrom.

The benzoxazine resin is anyone selected from the benzoxazine resins having the following structures, or a combination of at least two selected therefrom;

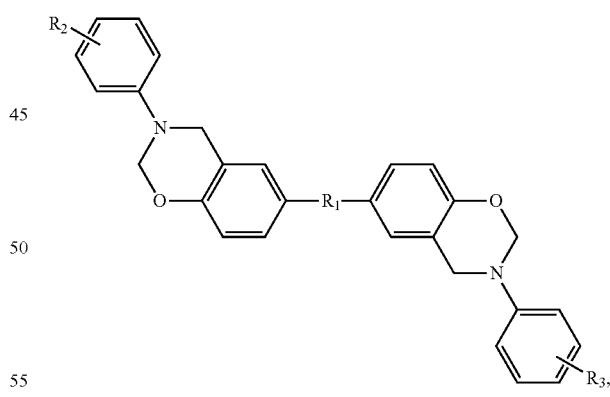

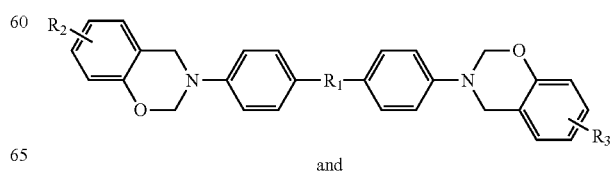

and

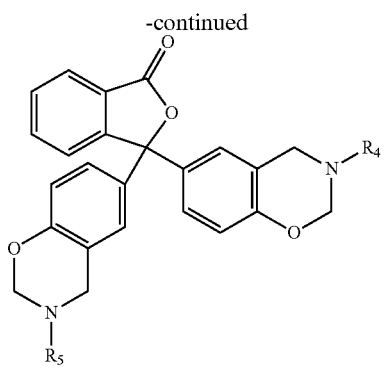

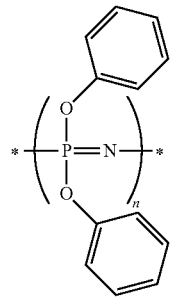

wherein n is a positive integer greater than 1.

As for the halogen-free resin composition of the present invention, the addition of phosphorus-nitrogen based compound has the advantage of increasing the flame retardancy of the halogen-free epoxy resin composition and the cured product thereof. The phosphorus-nitrogen based compound of the present invention as the flame retardant has primary advantage that the phosphorus-nitrogen based compound has no free hydroxyl group (—OH), so that the addition thereof will not have an adverse effect on the dielectric performances of such resin composition. In addition, such phosphorus-nitrogen based compound also had a high phosphorus content (13%), a thermal cracking temperature of higher than 350° C., better moisture-resistance stability and a low hygroscopicity, and have a better effect than general phosphorus-containing flame retardants conventionally used.

In order to further improve the flame retardancy of the halogen-free epoxy resin composition, the present invention may optionally add, besides the phosphorus-nitrogen based compound, the following halogen-free flame retardant selected from the group consisting of ammonium polyphosphate, tri(2-carboxyethyl)phosphine, tri(isopropylchloro) phosphate, trimethyl phosphate, dimethyl-methyl phosphate, resorcinol bis-xylyl phosphate, melamine polyphosphate, melamine cyanurate and tri-hydroxyethyl isocyanurate, or a combination of at least two selected therefrom.

The halogen-free epoxy resin composition further comprises from 20 to 100 parts by weight of a filler, such as 25, 30, 35, 40, 45, 50, 55, 60, 65, 70, 75, 80, 85, 90 or 95 parts by weight.

The filler is an organic and/or inorganic filler, and has primary functions of improving the dielectric performances, decreasing the coefficient of thermal expansion, improving the thermal conductivity and reducing the cost.

The inorganic filler is anyone selected from the group consisting of aluminum hydroxide, alumina, magnesium hydroxide, magnesium oxide, aluminum oxide, silica (including crystalline, molten and spherical silica), calcium carbonate, aluminum nitride, boron nitride, silicon carbide, titanium dioxide, zinc oxide, zirconium oxide, mica, boehmite, calcined talc, talcum powder, silicon nitride and calcined kaolin, or a mixture of at least two selected therefrom.

The organic filler is anyone selected from the group consisting of polytetrafluoroethylene powder, polyphenylene sulfide and polyether sulfone powder, or a mixture of at least two selected therefrom.

The filler in the present invention has a particle size of from 0.01 to 50 μm.

In order to make the filler homogeneously disperse in the halogen-free epoxy resin composition, a dispersant may also be added therein. The dispersant used therein is an amino wherein $R_2$ and $R_3$ are mono- or poly-substituted, and are each independently selected from the group consisting of hydrogen, methyl, allyl and formyl group; $R_1$ is anyone selected from the group consisting of —CH$_2$—, —O—, —C(CH$_3$)$_2$—, —SO$_2$—, —C(CF$_3$)$_2$—, —CH$_2$CH$_2$— and dicyclopentadiene, or a combination of at least two selected therefrom; $R_4$ and $R_5$ are each independently anyone selected from the group consisting of allyl, unsubstituted or substituted phenyl, unsubstituted or substituted alkyl having 1-8 carbon atoms and cycloalkyl having 1-8 carbon atoms, or a combination of at least two selected therefrom.

The styrene-maleic anhydride has a structural formula of:

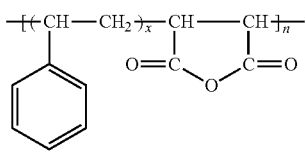 [SMILES: CC(CC1C(=O)OC(=O)C1C)c1ccccc1]

wherein x:n=0.8-19:1, preferably 1-15:1, further preferably 1-12:1.

The styrene-maleic anhydride has a number average molecular weight of 1000-50000, preferably 1500-45000 and further preferably 2000-40000.

Exemplary styrene-maleic anhydride includes maleic anhydrides with product names such as SMA-1000, SMA-2000, SMA-3000, EF-30, EF-40, EF-60 and EF-80.

The phosphorus-containing novolac is anyone selected from the group consisting of 9,10-dihydro-9-oxa-10-phosphaphenanthrene-10-oxide (DOPO) modified novolac resin, 1042, 5-dihydroxylphenyl)-9,10-dihydro-9-oxa-10-phosphaphenanthrene-10-oxide (DOPO-HQ) modified novolac resin, 10-(2,9-dihydroxylnaphthyl)-9,10-dihydro-9-oxa-10-phosphaphenanthrene-10-oxide (DOPO-NQ) modified novolac resin, or a mixture of at least two selected therefrom.

The phosphorus-nitrogen based compound of the present invention is a compound containing phosphorus and nitrogen atoms, preferably a phosphorus-nitrogen based compound having the following structure having flame retardant function. While the substrate formed by curing the halogen-free resin composition combusts, the phosphorus atoms in the phosphorus-nitrogen based compound will form coke-like phosphoric acid which covers on the substrate surface and blocks the continuous entry of air, so as to block the combustion;

silane coupling agent and/or epoxy silane coupling agent for improving the binding performance between the reinforcing materials such as inorganic and woven glass cloth, so as to achieve the object of homogeneous dispersion. Moreover, such coupling agents having a usage amount of 0.5-2% of the weight of filler that contain no heavy metals, and have no adverse effect on human bodies. If the usage amount is too high, it will speed up the reaction, and affect the storage time; if the usage amount is less, it has no effect of notably improving the binding stability.

The halogen-free epoxy resin composition further comprises a curing accelerator which is selected from imidazole accelerators, preferably anyone selected from the group consisting of 2-methyl imidazole, undecyl imidazole, 2-ethyl-4-methyl imidazole, 2-phenyl imidazole and 1-cyanoethyl-substituted imidazole, or a combination of at least two selected therefrom.

The wording "comprising/comprise(s)" in the present invention means further comprising other components than said components, wherein these other components endow the epoxy resin composition with different characteristics. In addition, the wording "comprising/comprise(s)" of the present invention may be replaced with "being" or "consisting/consist(s) of" in a closed manner.

For example, the epoxy resin composition further comprises various additives, specifically such as antioxidants, thermal stabilizers, antistatic agents, UV absorbers, pigments, colorants or lubricants and the like. These additives can be used alone, or in combination thereof.

In the present invention, the epoxy resin composition preferably comprises no amine curing agents. This is because that, although the introduction of amine curing agents can increase the cohesiveness of the substrate, it will decrease the heat resistance of the substrate and cannot meet the requirements on high multilayer application.

The second object of the present invention lies in providing a prepreg prepared by using the halogen-free epoxy resin composition, wherein the prepreg comprises a reinforcing material and the aforesaid halogen-free epoxy resin composition attached thereon after impregnation and drying.

The reinforcing material is selected from non-woven or woven glass fabric cloth.

The third object of the present invention lies in providing a printed circuit board comprising at least one overlapped prepreg as stated above.

The present invention further provides a copper-clad laminate prepared from the prepreg, wherein the copper-clad laminate comprises at least one overlapped prepreg and copper foils coated onto one or both sides of the overlapped prepreg. Each of the prepregs comprises a reinforcing material and the halogen-free epoxy resin composition attached thereon after impregnation and drying.

As compared with the prior art, the present invention has the following beneficial effects.

(1) The present invention discloses using 15-28 parts by weight of benzoxazine resin and 10-20 parts by weight of styrene-maleic anhydride to cure 60 parts by weight of epoxy resin, which can ensure the Df value stability of prepregs at different curing temperatures, while maintaining low dielectric constant and dielectric loss, and overcomes the shortcomings that the Df of the benzoxazine resin and styrene-maleic anhydride-cured epoxy resin system changes along with the curing temperatures.

(2) The present invention discloses using benzoxazine resin having flame retardancy as the curing agent, adding phosphorus-containing novolac and phosphorus-nitrogen based compound having a low water absorption to achieve synergistic flame retardancy effect with phosphorus and nitrogen, which greatly decreases the phosphorus content and increases the flame retardancy of the substrate, so as to make the substrate have a better moisture resistance.

(3) The prepregs and laminates prepared from such resin composition have comprehensive performances, such as low dielectric constant (1 GHZ, 3.9 or less), low dielectric loss, excellent flame retardancy (V-0 or V-1), heat resistance (Tg, DSC, 178° C. or more), cohesiveness (peeling strength being 1.25 N/mm or more), low water absorption (0.36% or less) and excellent moisture resistance, and overcome the shortcomings of the current halogen-free laminates, such as high dielectric constant, inefficient heat resistance and worse moisture resistance, and are suitable for use in halogen-free multilayer circuit boards.

EMBODIMENTS

The technical solution of the present invention is further stated by the following specific embodiments.

As for the resin composition for use in prepregs and laminates of the present invention, the peeling strength, glass transition temperature, flame retardancy, dip soldering resistance limit after two hours of PCT, water absorption and dielectric constant of substrates cured at 200° C. for 120 min were tested, and the dielectric loss performance was tested at different curing temperatures. The following examples provide further description.

Epoxy resin, benzoxazine, styrene-maleic anhydride, phosphorus-containing novolac, phosphorus-nitrogen based compound, filler and other auxiliaries were fed into a container, stirred and homogeneously mixed to make a glue. A solvent was used to adjust the solid content of the solution to 60 wt %-70 wt % to obtain a glue solution, i.e. the resin composition glue solution of the present invention. A glass fabric having 2116 electronic grade was impregnated with the glue, baked with an oven to prepare a prepreg. Six sheets of 2116 prepregs were covered by both sides with electrolytic copper foils having a thickness of 35 μm, vacuum-laminated by a thermocompressor, cured at 190° C., 200° C. and 210° C. for 120 min to obtain a copper-clad plate.

The components in the examples and comparison examples are stated as follows.

(A) Epoxy resin (A-1) NC-3000-H (Trade name from Japan Chemical)

(A-2) HP-7200H (Trade name from Dainippon Ink)

(B) Benzoxazine (B-1) D-125 (Trade name from Sichuan East wood Technology Group Co., Ltd)

(B-2) LZ8280 (Trade name from Huntsman Advanced Materials)

(C) Styrene-maleic anhydride oligomer: SMA-EF40 (Trade name from Sartomer)

(D-1) Dicyandiamide: DICY (Trade name from Ningxia Darong)

(D-2) Polyester: EXB-9460

(E) Phosphorus-containing novolac resin (E-1) XZ92741 (Trade name from DOW)

(E-2) LC-950 (Trade name from SHIN-A)

(F) Phosphorus-nitrogen compounds: SPB-100 (Trade name from Otsuka Chemical Corporation)

(G) Filler: molten silica

TABLE 1

|   | Example 1 | Example 2 | Example 3 | Example 4 | Example 5 | Example 6 | Example 7 | Example 8 | Example 9 | Com. Example 1 |
|---|---|---|---|---|---|---|---|---|---|---|
| A-1 | 60 | 60 | 60 | 60 |    | 30 | 60 | 60 | 60 | 60 |
| A-2 |    |    |    |    | 60 | 30 |    |    |    |    |
| B-1 | 15 | 23 | 28 | 23 |    |    | 20 | 25 | 23 | 10 |
| B-2 |    |    |    |    | 23 | 28 |    |    |    |    |
| C | 10 | 16 | 20 | 16 | 20 | 15 | 18 | 15 | 16 | 16 |
| E-1 |    |    |    | 18 |    |    |    |    | 18 | 18 |
| E-2 |    |    |    |    | 40 | 10 |    |    |    |    |
| F |    |    |    | 30 | 10 | 50 |    |    | 30 | 30 |
| G |    |    |    | 50 | 50 | 100 |    |    |    | 50 |

|   | Com. Example 2 | Com. Example 3 | Com. Example 4 | Com. Example 5 | Com. Example 6 | Com. Example 7 | Com. Example 8 |
|---|---|---|---|---|---|---|---|
| A-1 | 60 |    |    | 30 | 30 |    |    |
| A-2 |    | 60 | 60 | 30 | 30 | 60 | 60 |
| B-1 | 40 |    |    |    |    |    |    |
| B-2 |    | 23 | 23 | 28 | 28 | 23 | 23 |
| C | 16 | 5 | 40 | 15 | 15 | 20 | 20 |
| E-1 | 18 |    |    |    |    |    |    |
| E-2 |    | 18 | 40 | 5 | 50 | 40 | 40 |
| F | 30 | 10 | 10 | 50 | 50 | 5 | 60 |
| G | 50 | 50 | 50 | 100 | 100 | 50 | 50 |

TABLE 2

| Testing items | | Example 1 | Example 2 | Example 3 | Example 4 | Example 5 | Example 6 | Com. Example 1 | Com. Example 2 | Com. Example 3 |
|---|---|---|---|---|---|---|---|---|---|---|
| Tg(DSC) (° C.) | | 178 | 185 | 188 | 182 | 182 | 180 | 170 | 190 | 171 |
| Peeling strength (N/mm) | | 1.32 | 1.32 | 1.25 | 1.35 | 1.28 | 1.30 | 1.30 | 1.35 | 1.30 |
| Combustibility | | V-1 | V-1 | V-1 | V-0 | V-0 | V-0 | V-0 | V-0 | V-0 |
| PCT(min) | | >5 | >5 | >5 | >5 | >5 | >5 | >5 | >5 | >5 |
| PCT water absorption % | | 0.32 | 0.32 | 0.35 | 0.33 | 0.36 | 0.33 | 0.35 | 0.36 | 0.36 |
| Processability | | Good | Good | Good | Good | Good | Good | Good | Worse | Worse |
| Dielectric constant (1 GHz) | | 3.9 | 3.9 | 3.9 | 3.9 | 3.9 | 3.9 | 4.0 | 3.9 | 4.0 |
| Dielectric loss (1 GHz) | 190° C./120 min | 0.007 | 0.0063 | 0.0063 | 0.0063 | 0.0067 | 0.0065 | 0.0075 | 0.0063 | 0.008 |
| | 200° C./120 min | 0.007 | 0.0063 | 0.0063 | 0.0063 | 0.0067 | 0.0065 | 0.0075 | 0.0072 | 0.008 |
| | 210° C./120 min | 0.007 | 0.0063 | 0.0063 | 0.0063 | 0.0067 | 0.0065 | 0.0075 | 0.0080 | 0.008 |

TABLE 3

| Testing items | | Example 7 | Example 8 | Example 9 | Com. Example 4 | Com. Example 5 | Com. Example 6 | Com. Example 7 | Com. Example 8 |
|---|---|---|---|---|---|---|---|---|---|
| Tg(DSC) (° C.) | | 184 | 184 | 182 | 188 | 182 | 175 | 184 | 170 |
| Peeling strength (N/mm) | | 1.33 | 1.33 | 1.32 | 1.02 | 1.30 | 1.30 | 1.30 | 1.30 |
| Combustibility | | V-1 | V-1 | V-0 | V-1 | V-1 | V-0 | V-1 | V-0 |
| PCT(min) | | >5 | >5 | >5 | >5 | >5 | 4 | >5 | 4 |
| PCT water absorption % | | 0.32 | 0.32 | 0.32 | 0.40 | 0.32 | 0.41 | 0.36 | 0.36 |
| Processability | | Good | Good | Good | Good | Good | Good | Good | Worse |
| Dielectric constant (1 GHz) | | 3.9 | 3.9 | 3.9 | 3.9 | 3.9 | 3.9 | 3.9 | 3.9 |
| Dielectric loss (1 GHz) | 190° C./120 min | 0.0063 | 0.0063 | 0.0063 | 0.006 | 0.0065 | 0.0068 | 0.0067 | 0.0067 |
| | 200° C./120 min | 0.0063 | 0.0063 | 0.0063 | 0.0068 | 0.0065 | 0.0068 | 0.0067 | 0.0067 |
| | 210° C./120 min | 0.0063 | 0.0063 | 0.0063 | 0.0078 | 0.00654 | 0.0068 | 0.0067 | 0.0067 |

According to Tables 1-3:

According to Example 1 and Examples 2, 7, 8, it can be seen that the formulae obtained by optimizing with curing agents has a lower Df value and a high Tg.

According to Examples 2, 7, 8 and Example 3, it can be seen that, although the formulae optimized with curing agents has a lower Tg, it has a higher peeling strength and a lower water absorption. That is to say, it can be seen according to Examples 1-3, 7 and 8 that the formulae optimized with curing agents has better comprehensive performances.

According to a comparison of Example 2 and Examples 4 and 9, it can be seen that, although Tg is slightly reduced after the addition of phosphorus-containing novolac and phosphorus-nitrogen based compounds, it can be ensured that the flame retardancy can achieve V-0, and there is no effect on other performances. In addition, the addition of fillers has little effect on the substrate performance.

According to Example 4 and Comparison Examples 1-2, it can be seen that, when benzoxazine is in an amount less than 15 parts by weight, the Tg thereof is lower, and the dielectric performances are worse; when benzoxazine is in an amount higher than 28 parts by weight, the processability thereof is worse, and Df is unstable and increases along with the increase of the curing temperature, although it has a higher Tg.

According to Example 5 and Comparison Examples 3-4, it can be seen that, when styrene-maleic anhydride is in an amount less than 10 parts by weight, Tg is insufficient, and the dielectric loss performance is worse, which will affect the processability of the substrate; when the amount is higher than 20 parts by weight, the flame retardancy is insufficient although Tg can increase; the water absorption increases; the Df is unstable and will increase along with the increase of the curing temperature.

According to Example 6 and Comparison Examples 5-6, it can be seen that, when phosphorus-containing novolac is in an amount less than 10 parts by weight, the flame retardancy cannot achieve the V-0 level; when phosphorus-containing novolac is in an amount higher than 40 parts by weight, such amount can ensure the flame retardancy, but increase the water absorption of the substrate and decrease the Tg, and will affect the PCT performance of the substrate.

According to Example 5 and Comparison Examples 7-8, it can be seen that, when the phosphorus-nitrogen based compound is in an amount less than 10 parts by weight, the flame retardancy cannot achieve the V-0 level; when the phosphorus-nitrogen based compound is in an amount higher than 50 parts by weight, such amount can ensure the flame retardancy, but decrease the Tg, and will affect the PCT performance and processability of the substrate.

Comparison Example 9

Comparison Example 9 is Example 4 disclosed in CN 101684191B.

Comparison Example 10

Comparison Example 10 is Example 1 disclosed in CN103131131A.

Comparison Example 11

Comparison Example 11 is Example 2 disclosed in CN 103881302A.

TABLE 4

|  | Com. Example 9 | Com. Example 10 | Com. Example 11 |
|---|---|---|---|
| A-1 | 60 | 35 | 35 |
| A-2 |  | 25 | 25 |
| B-1 | 115 | 30 |  |
| B-2 |  |  | 42 |
| C | 42 | 6 | 18 |
| D-1 |  | 0.9 |  |
| D-2 |  |  | 12 |
| E-1 | 44 |  | 24 |
| E-2 |  |  |  |
| F |  | 21 |  |
| G |  | 21 | 31 |

TABLE 5

| Testing items | Com. Example 9 | Com. Example 10 | Com. Example 11 |
|---|---|---|---|
| Tg(DSC) (° C.) | 175 | 167 | 170 |
| Peeling strength (N/mm) | 1.27 | 1.38 | 1.32 |
| Combustibility | V-1 | V-0 | V-0 |
| PCT(min) | >5 | 3 | >5 |
| PCT water absorption % | 0.32 | 0.40 | 0.34 |
| Processability | Good | Good | Good |
| Dielectric constant (1 GHz) | 4.0 | 3.9 | 3.9 |
| Dielectric loss (1 GHz) 190° C./120 min | 0.006 | 0.009 | 0.006 |
| 200° C./120 min | 0.0068 | 0.009 | 0.0065 |
| 210° C./120 min | 0.0072 | 0.009 | 0.0072 |

According to Examples 1-9, it can be seen that the laminates prepared from the halogen-free resin composition of the present invention have better dielectric performances, the dielectric loss value will not change along with the increase of the curing temperature and can achieve the V-0 standard in the flame retardancy test UL-94. Thus, while ensuring the halogen-free flame retardancy, the laminates also have comprehensive performances, such as low dielectric constant, low dielectric loss, excellent heat resistance, cohesiveness and moisture resistance, and are suitable for use in halogen-free high multi-layer circuit boards. The prepregs and laminates prepared from the resin composition of the present invention have comprehensive performances, such as low dielectric constant, low dielectric loss, excellent flame retardancy, heat resistance, cohesiveness and moisture resistance, overcome the shortcomings of the current halogen-free laminates, such as insufficient heat resistance and worse moisture resistance and are suitable for use in halogen-free high multi-layer circuit boards.

The present invention discloses the detailed process via the aforesaid examples. However, the present invention is not limited by the aforesaid detailed process. That is to say, it does not mean that the present invention cannot be carried out unless the aforesaid detailed process is used. Those skilled in the art shall know that any improvement, equivalent replacement of various raw materials of the present invention, addition of auxiliary ingredients, selection of specific modes and the like all fall within the protection scope and disclosure of the present invention.

The invention claimed is:

1. A halogen-free epoxy resin composition, comprising 60 parts by weight of epoxy resin, from 20 to 25 parts by weight of benzoxazine resin, and from 15 to 18 parts by weight of styrene-maleic anhydride,
   wherein the epoxy resin is any one selected from the group consisting of biphenyl epoxy resin, and dicyclopentadiene epoxy resin, wherein the benzoxazine resin is any one selected from the benzoxazine resins having the following structures:

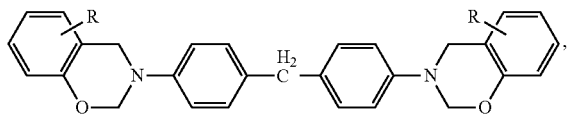

wherein R is H or CH$_3$, wherein the styrene-maleic anhydride has a structural formula of:

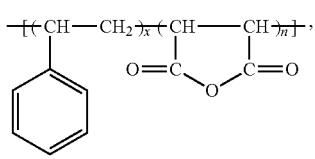 [SMILES: CC(CC1C(=O)OC(=O)C1C)c1ccccc1]

wherein x:n=4.

2. The halogen-free epoxy resin composition claimed in claim 1, wherein the halogen-free epoxy resin composition further comprises a halogen-free flame retardant selected from the group consisting of ammonium polyphosphate, tri(2-carboxyethyl)phosphine, tri(isopropylchloro)phosphate, trimethyl phosphate, dimethyl-methyl phosphate, resorcinol bis-xylyl phosphate, melamine polyphosphate, melamine cyanurate and tri-hydroxyethyl isocyanurate, or a combination of at least two selected therefrom.

3. The halogen-free epoxy resin composition claimed in claim 1, wherein the halogen-free epoxy resin composition further comprises from 20 to 100 parts by weight of a filler.

4. The halogen-free epoxy resin composition claimed in claim 3, wherein the filler is an organic or/and inorganic filler.

5. The halogen-free epoxy resin composition claimed in claim 4, wherein the inorganic filler is any one selected from the group consisting of aluminum hydroxide, alumina, magnesium hydroxide, magnesium oxide, silica calcium carbonate, aluminum nitride, boron nitride, silicon carbide, titanium dioxide, zinc oxide, zirconium oxide, mica, boehmite, calcined talc, talcum powder, silicon nitride and calcined kaolin, or a mixture of at least two selected therefrom, and the organic filler is any one selected from the group consisting of polytetrafluoroethylene powder, polyphenylene sulfide and polyether sulfone powder, or a mixture of at least two selected therefrom.

6. The halogen-free epoxy resin composition claimed in claim 3, wherein the filler has a particle size of from 0.01 to 50 μm.

7. The halogen-free epoxy resin composition claimed in claim 1, wherein the halogen-free epoxy resin composition comprises a curing accelerator which is any one selected from imidazole accelerators.

8. The halogen-free epoxy resin composition claimed in claim 7, wherein the curing accelerator is any one selected from the group consisting of 2-methyl imidazole, undecyl imidazole, 2-ethyl-4-methyl imidazole, 2-phenyl imidazole and 1-cyanoethyl-substituted imidazole, or a combination of at least two selected therefrom.

9. A prepreg comprising a reinforcing material and the halogen-free epoxy resin composition in claim 1 attached thereon after impregnation and drying.

10. A laminate, comprising at least one overlapped prepreg claimed in claim 9.

11. A printed circuit board, comprising at least one overlapped prepreg claimed in claim 9.

* * * * *